(12) United States Patent
Berckmans et al.

(10) Patent No.: US 9,807,981 B2
(45) Date of Patent: Nov. 7, 2017

(54) AUTOMATED MONITORING OF ANIMAL NUTRIMENT INGESTION

(71) Applicant: KATHOLIEKE UNIVERSITEIT LEUVEN, Leuven (BE)

(72) Inventors: Daniel Berckmans, Kessel-Lo (BE); Arda Aydin, Heverlee (BE); Claudia Bahr, Heverlee (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 129 days.

(21) Appl. No.: 14/780,648

(22) PCT Filed: Mar. 28, 2014

(86) PCT No.: PCT/BE2014/000015
§ 371 (c)(1),
(2) Date: Sep. 28, 2015

(87) PCT Pub. No.: WO2014/153626
PCT Pub. Date: Oct. 2, 2014

(65) Prior Publication Data
US 2016/0050888 A1 Feb. 25, 2016

(30) Foreign Application Priority Data
Mar. 28, 2013 (GB) .................................. 1305725.2

(51) Int. Cl.
*A01K 29/00* (2006.01)
*A01K 5/02* (2006.01)
(Continued)

(52) U.S. Cl.
CPC .............. *A01K 29/005* (2013.01); *A01K 5/02* (2013.01); *A01K 39/01* (2013.01); *A01K 39/02* (2013.01);
(Continued)

(58) Field of Classification Search
CPC . A01K 1/00; A01K 1/103; A01K 5/00; A01K 5/01; A01K 7/00; A01K 7/005; A01K 7/02
(Continued)

(56) References Cited

U.S. PATENT DOCUMENTS 5,008,821 A * 4/1991 Pratt ........................ A01K 5/02
119/51.01
5,010,851 A * 4/1991 Gvaryahu .............. A01K 15/02
119/174
(Continued)

FOREIGN PATENT DOCUMENTS

WO 01/67853 A2 9/2001

OTHER PUBLICATIONS

International Search Report from corresponding PCT Application No. PCT/BE2014/000015, dated Oct. 9, 2014.
(Continued)

*Primary Examiner* — Richard Price, Jr.
(74) *Attorney, Agent, or Firm* — Workman Nydegger

(57) ABSTRACT

The present invention relates to a system and method for monitoring in real time the nutriment intake (feed and/or water) of farm animals, including but not limited to poultry, turkeys, pigs and cows, based on the measurement and identification of the nutriment uptake sounds and/or the working of the nutriment supply system, while the presence and eating position of the animals is monitored by using real-time image analysis.

20 Claims, 9 Drawing Sheets

Figure 1:
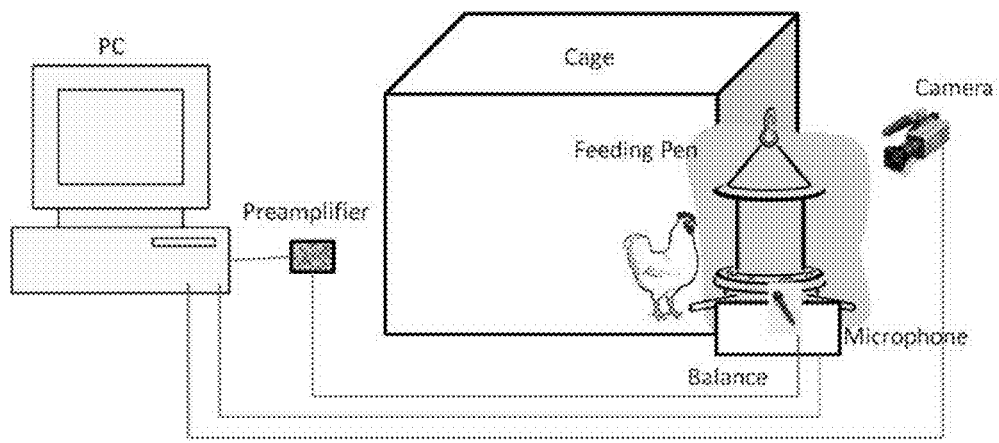

(51) Int. Cl.
  A01K 39/01 (2006.01)
  A01K 39/02 (2006.01)
  G01N 29/44 (2006.01)
(52) U.S. Cl.
  CPC ....... *G01N 29/44* (2013.01); *G01N 2291/028* (2013.01)
(58) Field of Classification Search
  USPC .................. 119/51.01, 51.02, 51.13, 57.7, 54
  See application file for complete search history.

(56) References Cited

U.S. PATENT DOCUMENTS

| | | | | |
|---|---|---|---|---|
| 5,901,660 | A * | 5/1999 | Stein | A01K 11/006 119/174 |
| 7,377,233 | B2 * | 5/2008 | Patton | A01K 11/008 119/712 |
| 7,681,527 | B2 * | 3/2010 | Pratt | A01K 29/00 119/174 |
| 7,827,935 | B1 * | 11/2010 | Addleman | A01K 1/0209 119/51.02 |
| 8,955,457 | B2 * | 2/2015 | Chen | A01K 61/80 119/230 |
| 2010/0332140 | A1 | 12/2010 | Joyce et al. | |

OTHER PUBLICATIONS

Aerts et al., "Dynamic Data-based Modelling of Heat Production and Growth of Broiler Chickens: Development of an Integrated Management System", Biosystems Engineering, 2003, vol. 84, p. 257-266.

Brandl et al., "Determination of Live Weight of Pigs from Dimensions Measured Using Image Analysis", Computers and Electronics in Agriculture, 1996, vol. 15, p. 57-72.

Exadaktylos et al., "Real-time Recognition of Sick Pig Cough Sounds", Computer and Agriculture, 2008, vol. 63, p. 207-214.

Galli et al., "Acoustic Monitoring of Chewing and Intake of Fresh and Dry Forages in Steers", Animal Feed Science and Technology, 2006, vol. 128, p. 14-30.

Gates et al., "Extracting Poultry Behaviour from Time-series Weigh Scale Records", Computer and Electronics in Agriculture, 2008, vol. 62, p. 8-14.

Gonzalez et al., Digitial Image Processing, Second Edition, Prentice Hall, Upper Saddle River, New Jersey, 2002, 190 pages.

Kashiha et al., "The Automatic Monitoring of Pigs Water Use by Cameras", Computers and Electronics in Agriculture, 2013, vol. 90, p. 164-169.

Lind et al., "Validation of a Digital Video Tracking System for Recording Pig Locomotor Behaviour", Journal of Neuroscience Methods, 2005, vol. 143, p. 123-132.

Madsen et al., "A Model for Monitoring the Condition of Young Pigs by their Drinking Behaviour", Computers and Electronics in Agriculture, 2005, vol. 48, p. 138-154.

Manteuffel et al., "Vocalization of Farm Animals as a Measure of Welfare", Applied Animal Behaviour Science, 2004, vol. 88, p. 163-182.

Otsu et al., "A Threshold Selection Method from Gray-Level Histograms", IEEE Transactions on Systems, Man, and Cybernetics, Jan. 1979, vol. SMC-9, No. 1, p. 62-66.

Sergeant et al., "Computer Visual Tracking of Poultry", Computers and Electronics in Agriculture, 1998, vol. 21, p. 1-18.

Silva et al., "Cough Localization for the Detection of Respiratory Diseases in Pig Houses", Computers and Electronics in Agriculture, 2008, vol. 64, p. 286-292.

Tillett et al., "Model-based Image Processing to Locate Pigs within Images", Computers and Electronics in Agriculture, 1991, vol. 6, p. 51-61.

Tu et al., "A Real-time Automated System for Monitoring Individual Feed Intake and Body Weight of Group Housed Turkeys", Computers and Electronics in Agriculture, 2011, vol. 11, p. 313-320.

Van Hirtum et al., "Objective Cough-Sound Recognition as as Biomarker for Aerial Factors", Transactions of the ASAE, American Society of Agriculture Engineers, 2004, vol. 47, p. 351-356.

Ungar et al., "Classifying Cattle Jaw Movements: Comparing IGER Behaviour Recorder and Acoustic Techniques", Applied Animal Behaviour Science, 2006, vol. 98, p. 11-27.

Xin et al., "Assessing Swine Thermal Comfort by Image Analysis of Postural Behaviors", Journal of Animal Science, 1999, vol. 77, p. 1-9.

Zhang et al., "Separation of Touching Grain Kernals in an Image by Ellipse Fitting Algorithm", Biosystems Engineering, 2005, vol. 92, p. 135-142.

* cited by examiner

AUTOMATED MONITORING OF ANIMAL NUTRIMENT INGESTION

FIELD OF THE INVENTION

The present invention present invention relates to a method and system for the automated monitoring of the amount of a nutriment taken up by an animal or group of animals feeding or drinking from a nutriment supply station within a given period of time.

BACKGROUND OF THE INVENTION

In modern day animal farming there is an increasing need for the automated livestock monitoring, in particular the (automated) collection of event-based behavioural responses of said animal, and the integration of these animal responses in livestock farming (Aerts et al., 2003, Biosystems Engineering 84, 257-266). In particular, computer and modern electronic technologies have been applied to monitor the behaviour, performance and welfare of farm animals.

In the last years, the analysis of farm sounds, particularly farm animal vocalisation, has gained increasing interest and a variety of attempts to decode the meaning has been made. In this context, Manteuffel et al. (2004; Applied Animal Behaviour Science 88 (1-2), 163-182) provide an overview of and problems associated with the vocalization of farm animals as a measure of animal welfare. Other approaches to evaluate and monitor animal welfare have examined the relationship between vocalisation or drinking behaviour and animal welfare (Exadaktylos et al, 2008, Comput. Electron. Agric., 63, 207-214; Madsen and Kristensen, 2005; Van Hirtum & Berckmans, 2004, Transactions of the ASAE 47, 351-356; Silva et al., 2008, Comput. Electron. Agric. 64, 286-292). In addition, research has been conducted on automation of welfare monitoring through water use estimation (Kashiha et al., 2013, Comput. Electron. Agric., 90, 164-169.), weight estimation (Brandi and Jorgensen, 1996, Comput. Electron. Agric., 15, 57-72), or locomotion analysis (Lind et al., 2005, J Neurosci Meth, 143, 123-132). Also, image processing has been used as well for monitoring the welfare of animals such as pigs (Xin, 1999, J. Anim. Sci., 77, 1-9), poultry (Sergeant et al., 1998, Comput. Electron. Agric., 21, 1-18), dairy cows, etc.

In addition to pig vocalisation, a lot of research on poultry behaviour and welfare related to sound vocalisation is presented in previous literature. The question of how management or environmental stimuli may influence poultry behaviour and/or well-being is of considerable importance for fundamental studies of behavioural response to stimuli, and as a means of assessing appropriate management and environmental designs for commercial production. One means of assessing bird response to stimuli involves careful analysis of characteristics of individuals or groups over time. Monitoring individual behaviour during research trials is typically performed with some type of video imaging system. For poultry, behavioural activities are categorized into events such as eating, drinking, preening, resting, and stereotype activities directed at different targets. This assessment methodology is time-consuming, hence costly, tedious and prone to errors, even with modern commercially available research systems that compile the statistics semi-autonomously. For this purpose, individual bird feeding statistics and stereotyped pecking behaviour from time-series recordings of feed weight were developed and compared to video observations (Gates and Xin, 2008, Comput. Electron. Agric., 62, 8-14). In another study, for turkey breeding, a structured query language (SQL) database management system was developed by Xuyong et al., 2011, Comput. Electron. Agric., 75, 313-320) to record and manage the dynamic feed intake measured by weighing scale and body weight gain data of individual birds. In other studies, animal behaviour was videotaped and chewing sound was recorded using a microphone attached to the steers' foreheads by Galli et al., 2005, Animal Feed Sci Technol, 128, 14-30) to evaluate acoustic analysis as a means to monitor and quantify chewing behaviour, and to estimate DM (dry matter) intake of forages with a wide range of water and fibre content. In another study, two methods (the IGER Behaviour Recorder (IBR) and acoustic monitoring (ACM)) for the detection and classification of jaw movements in grazing dairy cattle were compared by Ungar and Rutter, 2005, Appl Animal Behaviour Sci, 98, 11-27), wherein sound was detected by a microphone mounted against the cow's forehead with signals transmitted to a camcorder. Although these sound based methods may work with cattle, it is not possible to use it with 100,000 chickens in a broiler house.

Thus, in general, there remains a need, particularly in livestock farms, to have a reliable identification of animal nutriment (feed and water) intake, as this provides information on animal welfare and is also vital to reach a sound financial operation of the farm. Indeed, a reliable identification of feed intake is important to reach the right feed conversation rate, to calculate the waste of the food in each pen, to define the eating period and to define the dynamic feeding behaviour of the animals.

SUMMARY OF THE INVENTION

The inventors developed a system and method for monitoring the consumption or intake of a nutriment (feed and/or water intake and/or feeding or drinking behaviour) by an animal or group of animals. The system and method of the present invention are particularly suited for monitoring the nutriment intake of a livestock animal, such as a pig or a cow, and more particularly of a farm bird, such as chicken or turkey. The method and system of the present invention implement a sound or vibration detection and recognition technique to measure and identify nutriment uptake signals, such as sounds or vibrations, preferably resulting from a nutriment uptake action of an animal feeding or drinking from a nutriment supply station. Optionally, information on the presence, position and movements of animals within the vicinity of the nutriment supply station can be combined with the analysis of said sound or vibration data to further improve the estimation of the nutriment intake by monitoring how many animals are located at the nutriment supply station and whether the animals are in an eating or drinking location and/or position.

Thus, the present invention provides a novel, simple, noninvasive and inexpensive method for acquiring and applying information, preferably in real time, to assess the nutriment intake over a period of time, particularly feed and/or water intake, of an animal by detecting a nutriment uptake related signal, particularly a vibration, a sound, such as an impact sound, or another acoustic signal, wherein said signal is emitted as a result of the animal taking up a nutriment from a nutriment supply station. In contrast to other solutions described in literature, in the method of the present invention the nutriment uptake signal, for instance a nutriment uptake associated sound, is captured using a suitable sensor, for instance a microphone, located in the proximity of the nutriment supply station, preferably integrated in or attached to the nutriment supply station, without the need for sensors attached to or otherwise associated with the individual animal.

Optionally, the method of the present invention further involves the use of a system for detecting the presence and position of an animal at the nutriment supply system, preferably at the moment said nutriment uptake signal is detected. More particularly the method of the present invention may involve the use of an automated image monitoring system comprising at least one still or video camera, which in conjunction with a computing means allows detecting the presence and position of an animal at the nutriment supply system. Preferably, said camera is pointed at the nutriment supply station, preferably arranged in such a way as to provide a top-view image of the nutriment supply system and the nearby animal or animals. Advantageously, in this way, information is provided about the presence and position of animals near the nutriment supply station, including but not limited to the number of animals at the nutriment supply station, and the duration of the nutriment uptake or nourishment period as estimated based on for instance the duration of the presence of the animals in the immediate vicinity of the nutriment supply station. Preferably, the presence and position of an animal or group of animals at the nutriment supply system, such as the closeness of the at least one animal to the nutriment supply system and the direction from which it/they approach, is monitored using image analysis. Said image analysis typically comprises the steps of subtraction of the background and determination of threshold size of objects to distinguish the animals (so that only animals are detected). By applying a segmentation algorithm, animals are separated in the captured image and the duration the animal stays at the feeder or water supply system can be calculated.

Optionally, the method of the present invention further comprises the step of generating an alert or signal to the farmer or controller and/or to an animal within the vicinity of the nutriment supply station. Such signal or alert may for instance be generated when the nutriment uptake by an animal or group of animals within a given period of time exceeds or remains below a certain threshold.

The method of the present invention may further comprise the step of controlling, particularly in an automated manner; the provision of said nutriment to said at least one animal.

Preferably, the method of the present invention involves the use of a nutriment uptake signal that is a sound signal identified by analyzing sound data captured in the immediate vicinity or on the feed supply station. The analysis and identification of said nutriment uptake sound signal comprises a sound extraction step and a sound recognition step. Preferably, the extraction of sound information from the sound signal captured by the one or more sound sensors, preferably one or more microphones, comprises calculating the energy of the sound signal; calculating the square root of the sum of the energy and calculating the moving average of the result to get a smoothed estimate of the envelope of the initial signal.

In a particular embodiment the method of the present invention is used for the monitoring of the nutriment intake of farm bird animals, wherein said nutriment uptake signal results from the pecking of said farm bird when taking up a nutriment from a nutriment supply station. Preferably, said nutriment is a particulate feed supplied to the birds in a feeding pan (nutriment supply station), wherein said nutriment uptake signal is a sound signal resulting from the pecking of said farm bird when taking up feed from said feeding pan. More preferably, said nutriment uptake signal is an impact sound signal emitted through said feeding pan as a result of the pecking of said farm bird when taking up feed from said feeding pan. Typically, said impact sound signal is detected by analyzing the impact sound signals emitted through said feeding pan as captured using a suitable sensor, such as for instance a microphone attached to the feeding pan.

Another object of the present invention provides a computer based system for monitoring the consumption of a nutriment comprising (i) at least one means for sensing a nutriment uptake of at least one animal and/or a working of a nutriment supply station, wherein said sensing means is located in the proximity of the nutriment supply station, preferably attached to said nutriment supply station; (ii) a processing unit adapted to analyse and/or identify said sensed input, in particular said nutriment uptake signal, preferably a sound or vibration signal, or the working of said nutriment supply station. Preferably, said processing unit is adapted to calculate the nutriment intake (per unit of time) of the at least one animal based on the nutriment uptake signal data.

Preferably, said means for sensing a nutriment uptake or the working of a nutriment supply station is an accelerometer, a laser vibrometer, load cell or a microphone or another sensor suitable for capturing vibration and/or acoustic signals.

Preferably, the computer system according to the present invention further comprises means for monitoring the presence and position of the at least one animal at the nutriment supply station, such as the closeness of the animal or group of animals to the nutriment supply system and the direction from which an animal approaches. More preferably, said means to monitor the presence and position of an animal at the nutriment supply system is a means to capture images of the at least one animal located at or in the proximity of the nutriment supply system, most preferably said means comprises a camera arranged to provide a top-view image the animal or group of animals at the nutriment supply system. Typically, the processing unit of said computer based system is adapted to perform the image analysis and, more preferably, it is adapted to calculate the nutriment intake of said at least one animal (per unit of time) by combining the image analysis data with the sound analysis data.

Preferably, the computer based system according to the present invention further comprises means to perform the nutriment uptake signal and image analysis in real time, such as a processing unit.

Another object of the present invention provides a computer program product that includes code segments that when executed on a computer based system of the present invention implements any of the different method embodiments of the present invention described above. Another object of the present invention provides a machine readable storage medium or data carrier storing said above computer program product. Yet another object of the present invention relates to the transmission of said computer program product.

DESCRIPTION

Legend of the Figures

FIG. 1. shows the laboratory setup for sound recordings of an individual chicken.

Figure 2:
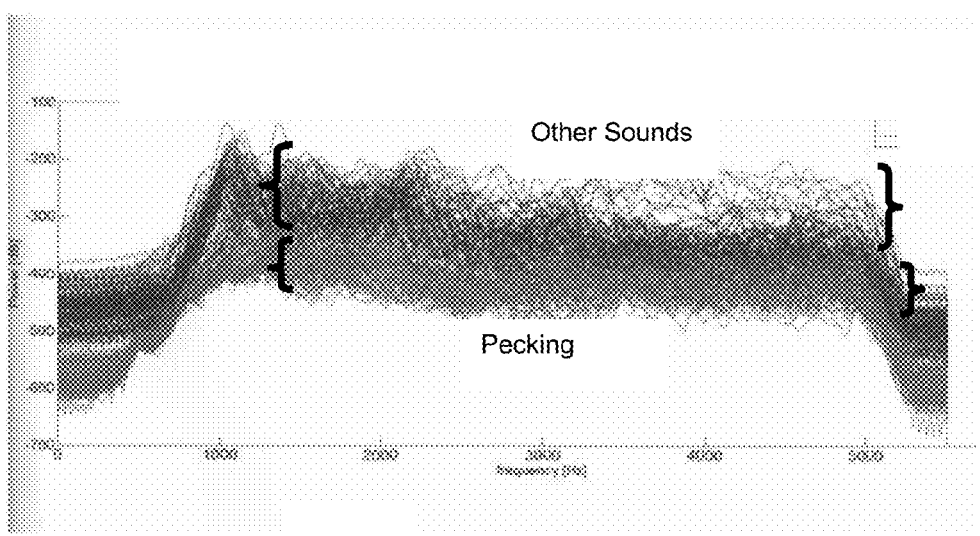

FIG. 2. shows the filtered sound signal between 1 kHz and 5 kHz.

Figure 3:

FIG. 3. shows the flowchart for the proposed signal processing procedure.

Figure 4:
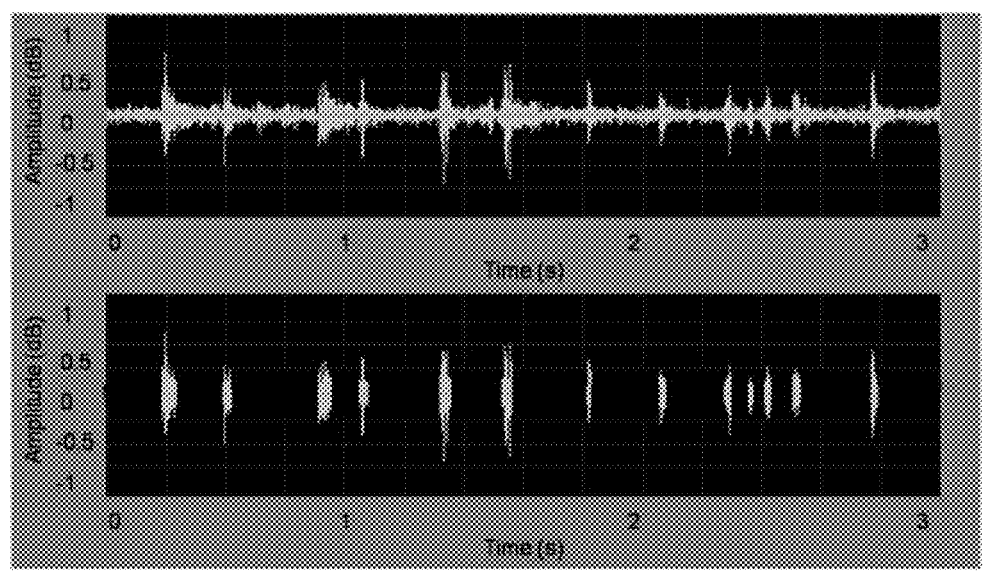

FIG. 4. presents a continuous recording of sounds (top) and the individual pecking sounds that are extracted by the system (bottom).

Figure 5:
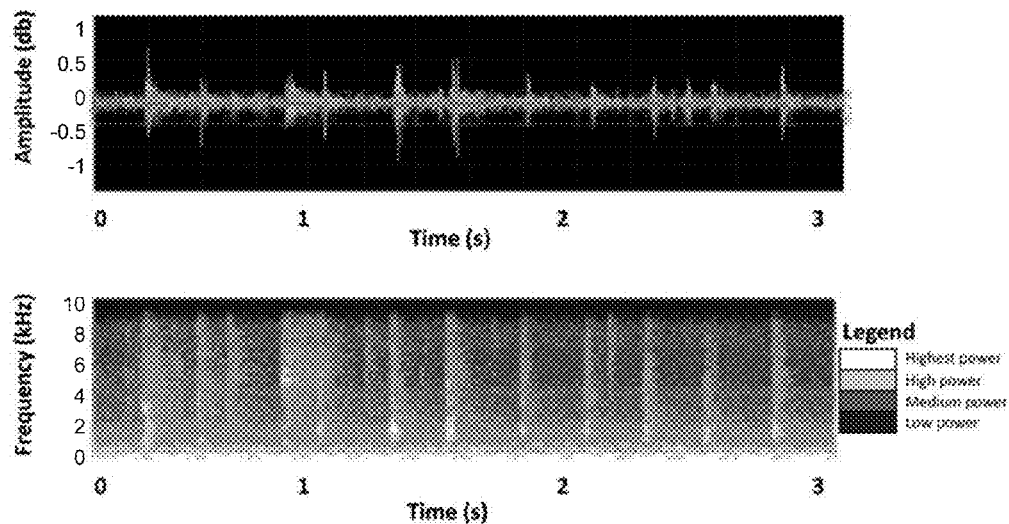

FIG. 5. shows the spectrogram of a continuous sound (consisting of 13 pecking hits) represented in time domain (above) and in frequency domain (below).

Figure 6:
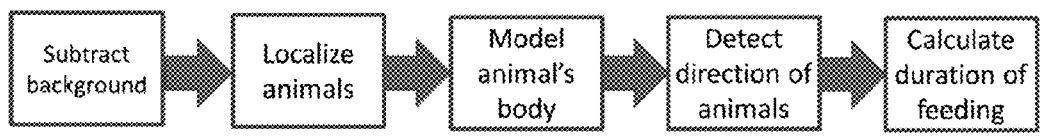

FIG. 6. shows the processing steps of animals image while feeding

Figure 7:

FIG. 7. shows the top view image of a feeder in a broiler house

Figure 8:
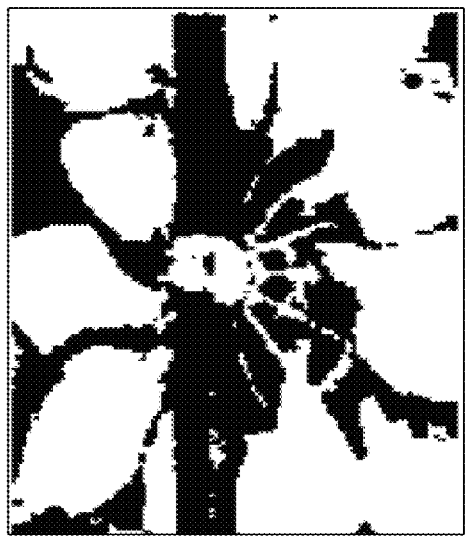

FIG. 8. shows the background subtracted image of broilers at the feeder

Figure 9:
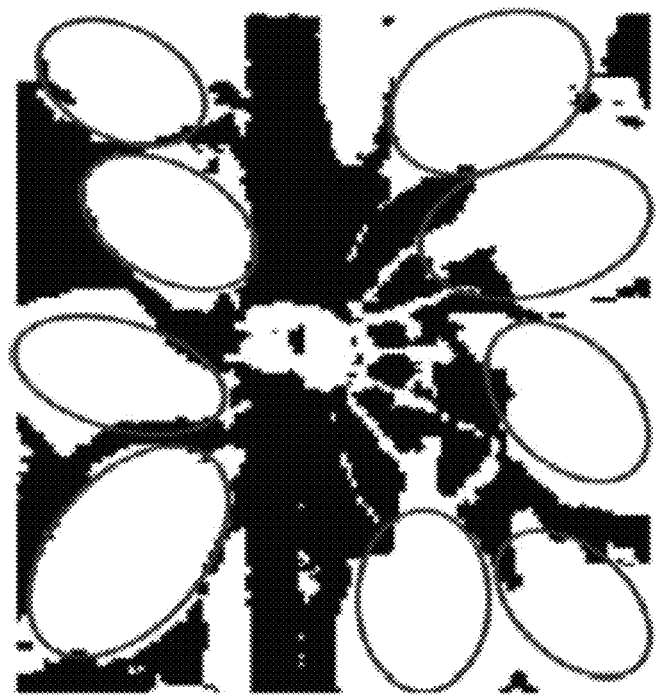

FIG. 9. shows the Ellipses fitted to broilers in the binary image

Figure 10:
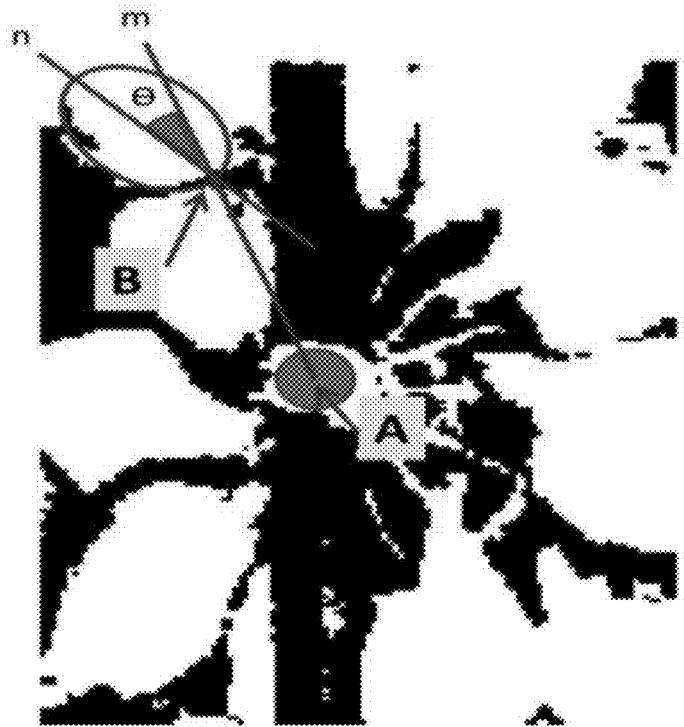

FIG. 10. Geometrical variables to set a criterion for a feeder visit. "A" is the center of the feeder. B is the closest intersection point of the ellipse's perimeter and its major axis (line n) to point A. θ is the angle between lines n and m (which passes through points A and B)

Figure 11:
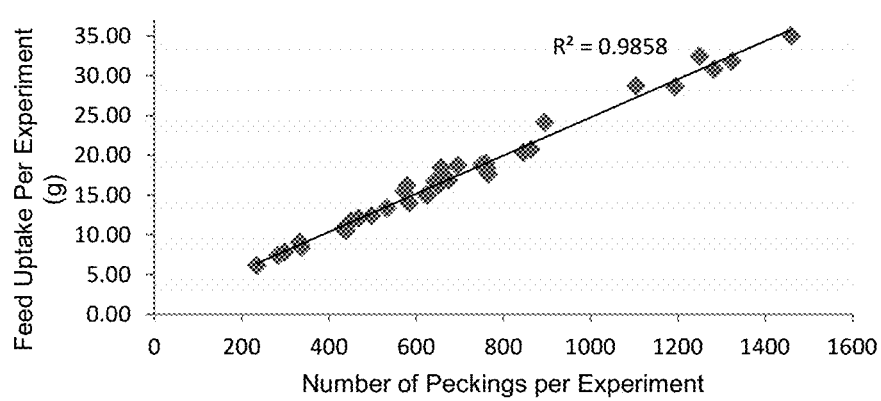

FIG. 11. The relation between feed uptake and number of peckings of chickens per experiment.

Figure 12:
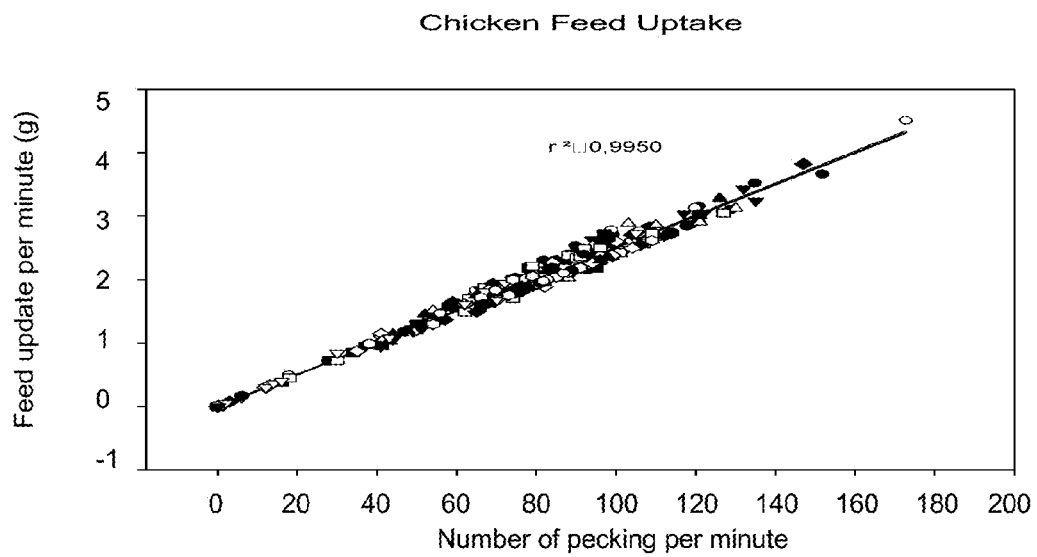
Figure 13:
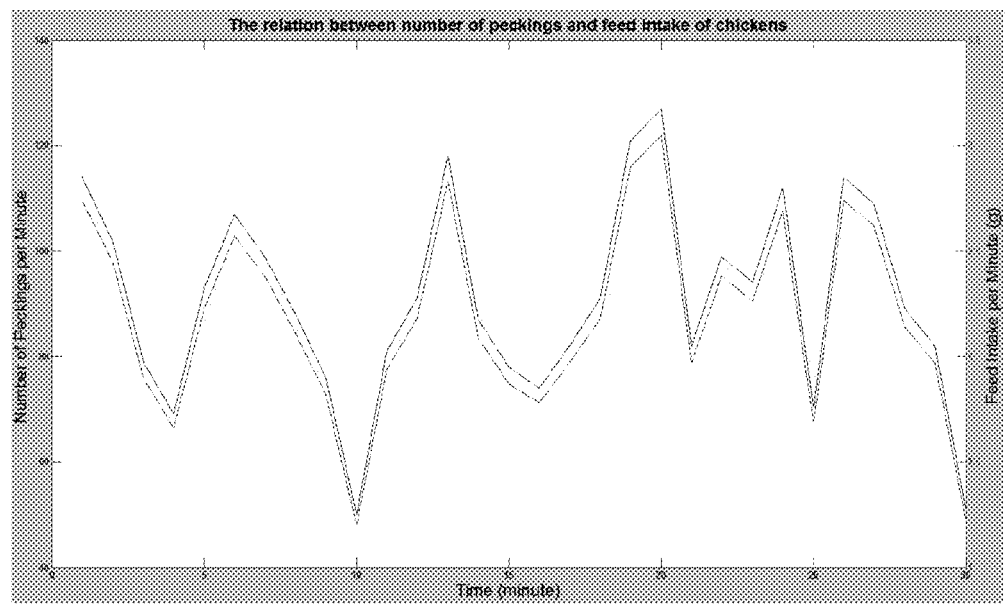

FIG. 12. The correlation between feed uptake per minute and number of peckings per minute FIG. 13. An example of the relation between number of peckings and feed intake of chickens.

Figure 14:
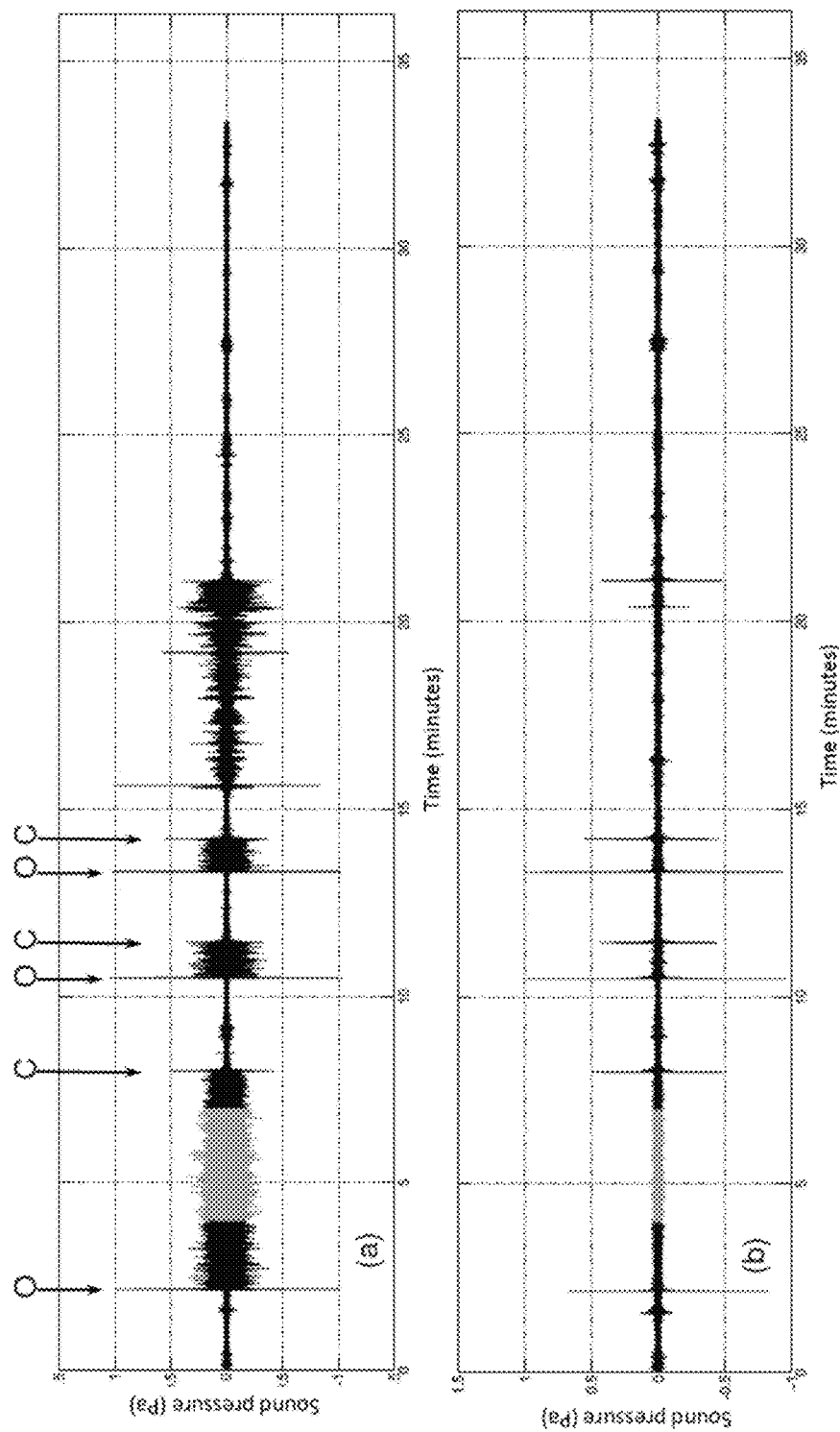

FIG. 14. Time signal of the recorded sound in microphone 1, resp. microphone 2 (open and close clicks are clearly visible and audible)

Figure 15:
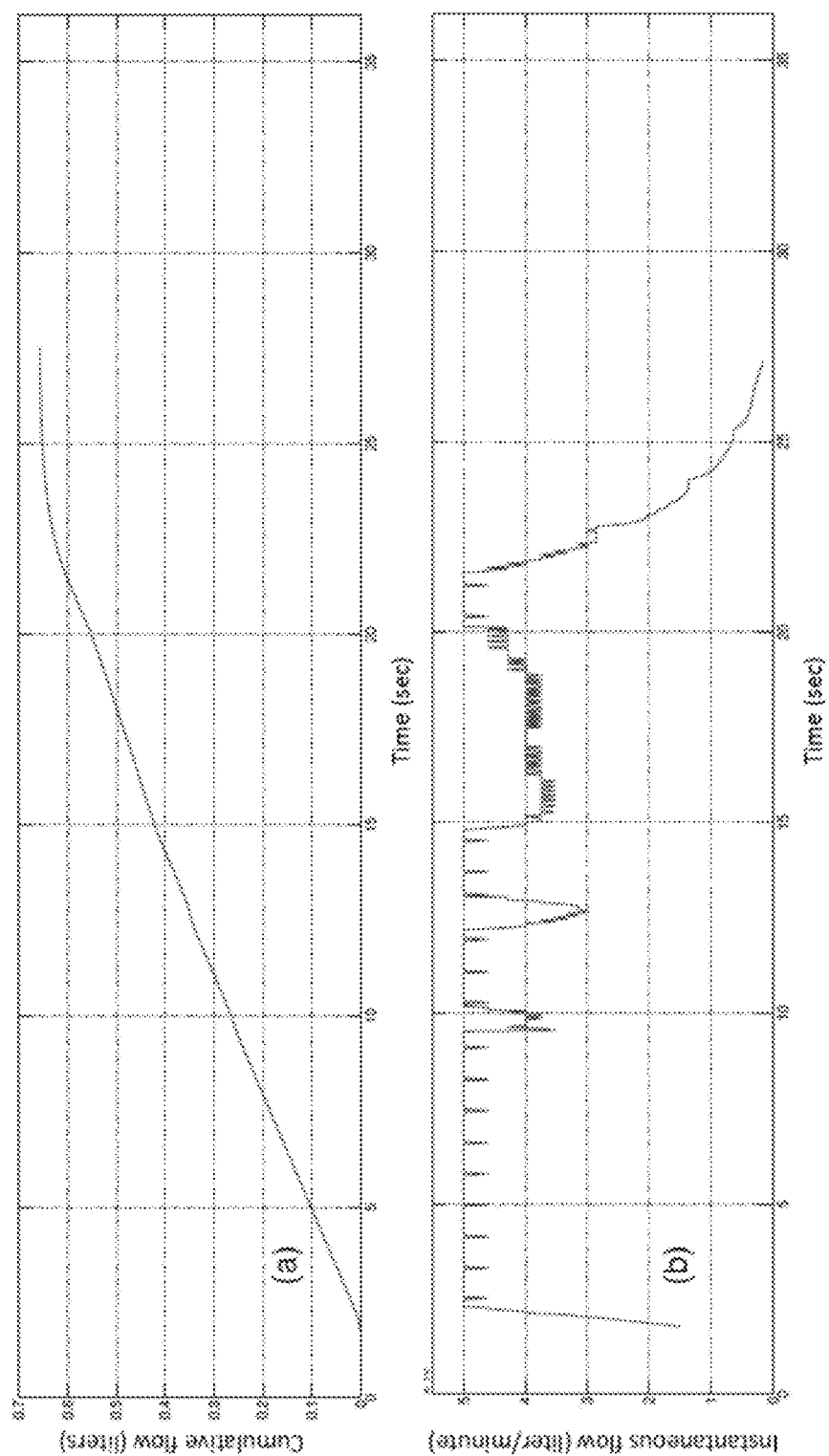

FIG. 15. Cumulative water flow through the Honsberg (water flow meter) sensor, as well as the instantaneous water flow through the sensor.

Figure 16:
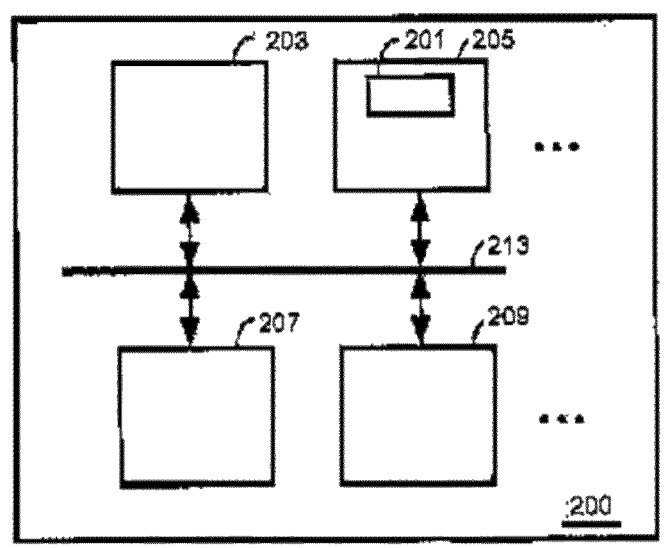

FIG. 16 schematically represents a computing system (e.g. PDA, laptop, PC, . . . ) for use with the present invention.

DETAILED DESCRIPTION

The present invention will be described with respect to particular embodiments and with reference to certain drawings. The skilled person will readily understand that the invention is not limited by the detailed features of those specific embodiments and, in particular, various modifications and developments may be made while still resting within the scope of the invention as defined in the appended claims. The drawings described are only schematic and are non-limiting. In the drawings, the size of some of the elements may be exaggerated and not drawn on scale for illustrative purposes.

The present invention is based on the finding that certain characteristic signals, referred to as nutriment uptake signals, are emitted when an animal or group of animals, such as farm animals, are feeding or drinking from a nutriment supply station. Considering that these signals originate from the impact exerted by the animals on the nutriment supply station during feeding or drinking, these nutriment uptake signals are preferably vibrations of the nutriment supply station or sounds, preferably impact sounds emitted through the feed supply station, resulting from said impact. Surprisingly, the inventors observed that the number of these signals within a given period of time correlated strongly with the amount of nutriment taken up from the nutriment supply station within that period of time. This observation led to the method and system of the present invention, which allow estimating the nutriment uptake by an animal or group of animals from a nutriment supply station over a period of time by the identification and counting of said nutriment uptake signals emitted during said time period as a result of the animal or group of animals feeding or drinking from said nutriment supply station. Preferably, the identification and counting of said nutriment uptake signals is done in an automated manner.

Thus in a first object the present invention provides an automated method for monitoring the amount of a nutriment taken up by an animal or group of animals feeding or drinking from a nutriment supply station wherein said method comprises the steps of:

a) acquiring sound and/or vibration data, wherein said vibration data is preferably data on the vibration of said nutriment supply station and/or wherein said sound data is preferably data on the impact sounds transmitted through said feed supply station;

b) analyzing said vibration and/or sound data, preferably impact sound data, in order to identify and count individual signals, referred to as nutriment uptake signals, resulting from a nutriment uptake action of an animal feeding or drinking from said nutriment supply station; and c) extrapolating the amount of nutriment taken up by said animal or group of animals within a given period of time based on the number of nutriment uptake signals recorded over said same period of time. This extrapolation typically involves the use of data from preceding experiments wherein for a given type of nutriment, a given type of nutriment supply system and a given species and type of animal or animals the correlation between the frequency of occurrence of the nutriment uptake signal and the amount of nutriment taken in by the animal or animals is established within a given time interval.

In case the method of the present invention involves the identification and counting of a nutriment uptake signal that is a sound signal, the method requires the use of a means for acquiring the relevant sound data. Said sound data may be acquired or recorded using one or more sound sensors or sound recording devices, such as one or more microphones. Preferably, said one or more sound sensors are located at or in proximity of the nutriment supply station, such as within a distance of at most 10, 20, 30, 40, 50, 60, 70, 80, 90, 100 cm of the nutriment supply station, more preferably said sound sensor or sensors are attached to the nutriment supply station, most preferably to the part of said nutriment supply system that is impacted by a nutriment uptake action of an animal feeding or drinking from said nutriment supply station. The sound sensor unit may include any known type of sound sensor for sensing a nutriment uptake sound and for converting them to electrical signals. For example, the sound sensor could be a (diaphragm-type) microphone, a piezoelectric device, or any other sound-to-electrical transducer. The sound sensor unit or processing unit may further include a filter for passing a predetermined signal bandwidth, an amplifier for amplifying the signal, and/or a data processor for processing the electrical signals produced by the sound detector. The analysis and identification of said nutriment uptake sound signal, preferably impact sound signal, comprises a sound extraction step and a sound recognition step. Preferably, the extraction of sound information from the sound signal captured by the one or more sound sensors, such as one or more microphones, comprises calculating the energy of the sound signal; calculating the square root of the sum of the energy and calculating the moving average of the result to get a smoothed estimate of the envelope of the initial signal.

In case the method of the present invention involves the identification and counting of a nutriment uptake signal that is a vibration signal detected on the nutriment supply station, the method requires the use of a means for acquiring data on the vibration of the nutriment supply system. Suitable sensor for acquiring such vibration data are for instance an accelerometer mounted on the nutriment supply station, a laser vibrometer pointing at the nutriment supply station or a load cell mounted on the nutriment supply station.

Preferably, the detection and analysis of said nutriment uptake signal and the extrapolation of the nutriment intake is performed in real-time or semi-real time, wherein fragments of data are recorded and processed in segments.

Optionally, the method according to the present invention comprises monitoring and/or identifying the presence and position of said animal or group of animals within the vicinity of the nutriment supply station, preferably at the moment said nutriment uptake signal is detected. Preferably, the presence and position of an animal or animals at the nutriment supply station is identified and/or monitored using a camera capturing images of the nutriment supply station and/or its vicinity and means for analyzing the images captured by said camera. More particularly the method of the present invention may involve the use of an automated image monitoring system comprising at least one still or video camera, which in conjunction with a computing means allows detecting the presence and position of an animal at the nutriment supply system. Preferably said camera is pointed at the nutriment supply system, preferably arranged in such a way as to provide a top-view image of the nutriment supply system and the nearby animal or animals. Advantageously, in this way, information is provided about the presence and position of animals near the nutriment supply station, including but not limited to the number of animals at the nutriment supply station, and the duration of the nutriment uptake or nourishment period as estimated based on for instance the duration of the presence of the animals in the immediate vicinity of the nutriment supply station. Preferably, the presence and position of an animal or group of animals at the nutriment supply system, such as the proximity to the nutriment supply system and the direction from which it/they approach, is monitored using image analysis. Said image analysis typically comprises the steps of subtraction of the background and determination of threshold size of objects to distinguish the animals (so that only animals are detected). By applying a segmentation algorithm, animals are separated in the captured image and the duration the animal stays at the feeder or water supply system can be calculated. Preferably, the analysis of the image data is combined with the analysis of said vibration and/or impact sound data in order to improve the accuracy of the nutriment uptake estimation. For instance, it may improve the accuracy when a detected nutriment uptake signal is ignored in case the analysis of the image data indicates that no animals are present at the nutriment supply station. Preferably, the detection and analysis of said nutriment uptake signal, the combination thereof with the image analysis data and the extrapolation of the nutriment intake is performed in real-time or semi-real time, wherein fragments of data are recorded and processed in segments.

The method of the present invention may be used for estimating the intake of different types of nutriments, including but not limited to solid feeds, particulate feeds, liquid feeds (milk) or water. Furthermore, the method of the present invention can be used in conjunction with different types of nutriment supply stations, including but not limited to a feeding pan (poultry), a trough or manger (cattle, horses, pigs) or a water or milk (calves) supply system.

Optionally, the method of the present invention further comprises the step of generating an alert or signal to the farmer or controller and/or to an animal within the vicinity of the nutriment supply station. Such signal or alert may for instance be generated when the nutriment uptake by an animal or group of animals within a given period of time exceeds or remains below a certain threshold.

The method of the present invention may further comprise the step of controlling, particularly in an automated manner; the provision of said nutriment to said at least one animal.

In a particular embodiment the method of the present invention is used for the monitoring of the nutriment intake of farm bird animals, wherein said monitored nutriment uptake signal is a signal resulting from the pecking of said farm bird when taking up a nutriment from a nutriment supply station. Preferably, said nutriment is a particulate feed supplied to the birds in a feeding pan, wherein said nutriment uptake signal is a sound signal, preferably an impact sound transmitted through said feeding pan or a vibration of the feeding pan, resulting from the pecking of said farm bird when taking up feed from said feeding pan. More preferably, said nutriment uptake signal is an impact sound signal emitted through said feeding pan as a result of the pecking of said farm bird when taking up feed from said feeding pan. Typically, said impact sound signal is detected by analyzing the impact sound signals emitted through said feeding pan as captured using a suitable sensor, such as for instance a microphone, preferably attached to the feeding pan. Alternatively, said nutriment uptake signal is a vibration of said feeding pan as a result of the pecking of said farm bird when taking up feed from said feeding pan. Typically, said vibration signal is detected by analyzing the vibrations of said feeding pan as captured using a suitable sensor, such as an accelerometer, laser vibrometer or load cell. Optionally, the method for monitoring the uptake of a nutriment by farm birds according to the present invention further involves monitoring and/or identifying the presence and position of a bird or group of birds within the vicinity of the nutriment supply station as previously described.

In a second object the present invention provides a system for monitoring the uptake of a nutriment by an animal or group of animals according to the method as described above wherein said system comprises
   a) means for acquiring sound and/or vibration data, wherein said vibration data is preferably data on the vibration of said nutriment supply station and/or wherein said sound data is preferably data on the impact sounds transmitted through said feed supply station;
   b) a processing unit adapted to (i) analyse said acquired vibration or sound data, preferably impact sound data, in order to identify and count individual signals, referred to as nutriment uptake signals, resulting from a nutriment uptake action of an animal feeding or drinking from said feed supply station and (ii) to extrapolate the amount of nutriment taken up by said animal or group of animals within a given period of time based on the number of nutriment uptake signals recorded over said same period of time. This extrapolation typically involves the availability in computer readable format of data from preceding experiments wherein for a given type of nutriment, a given type of nutriment supply system and a given species and type of animal or animals the correlation between the frequency of occurrence of the nutriment uptake signal and the amount of nutriment taken in by the animal or animals is established within a given time interval.

Suitable means for the acquisition of said sound data required for the identification and counting of a nutriment uptake signal may be any type of sound sensor or sound recording device, such as one or more microphones. Preferably, said sound sensor is located at or in proximity of the nutriment supply station, such as within a distance of at most 10, 20, 30, 40, 50, 60, 70, 80, 90, 100 cm of the nutriment supply station, more preferably said sound sensor or sensors are attached to the nutriment supply station, most preferably said one or more sensors are attached to the part of said nutriment supply system that is impacted by a nutriment uptake action of an animal feeding or drinking from said nutriment supply station. The sound sensor unit may include any known type of sound sensor for sensing a sound and for converting the sound signal to an electrical signal. For example, the sound sensor could be a (diaphragm-type) microphone, a piezoelectric device, or any other sound-to-electrical transducer. The sound sensor unit or processing unit may further include a filter for passing a predetermined signal bandwidth, an amplifier for amplifying the signal, and/or a data processor for processing the electrical signals produced by the sound detector. The analysis and identification of said nutriment uptake sound signal, preferably impact sound signal, as performed in said processing unit comprises a sound extraction step and a sound recognition step. Preferably, the extraction of sound information from the sound signal captured by the one or more sound sensors, preferably one or more microphones, comprises calculating the energy of the sound signal; calculating the square root of the sum of the energy and calculating the moving average of the result to get a smoothed estimate of the envelope of the initial signal.

Suitable means for the acquisition of said vibration data required for the identification and counting of a nutriment uptake signal are for instance an accelerometer mounted on the nutriment supply station, a laser vibrometer pointing at the nutriment supply station or a load cell mounted on the nutriment supply station.

Optionally, the system according to the present invention comprises means for monitoring and/or identifying the presence and position of an animal or group of animals within the vicinity of the nutriment supply station. Preferably, said means for monitoring and/or identifying the presence and position of an animal or animals at the nutriment supply station comprises a camera capturing images of the nutriment supply station and/or its vicinity and means for analyzing the images captured by said camera. More particularly said means for monitoring and/or identifying the presence and position of an animal or animals at the nutriment supply station comprise the use of an automated image monitoring system comprising at least one still or video camera, which in conjunction with a computing means allows detecting the presence and position of an animal at the nutriment supply system. Preferably said camera is pointed at the nutriment supply system, preferably arranged in such a way as to provide a top-view image of the nutriment supply system and the nearby animal or animals. Said image analysis typically comprises the steps of subtraction of the background and determination of threshold size of objects to distinguish the animals (so that only animals are detected). By applying a segmentation algorithm, animals are separated in the captured image. The vision system or image capture device may comprise a webcam or camera, possibly a low cost webcam or a camera with a rather low frame rate of 5 to 30 frames per second depending on requested refresh rate, accuracy and available processing resources. Data of the camera(s) can be transmitted to the processing unit by digital or analogue cables or wireless and sent to a processing unit through a video capturing interface. Videos can be buffered or processed and deleted immediately.

Optionally, the system of the present invention further comprises means for generating an alert or signal to the farmer or controller and/or to an animal within the vicinity of the nutriment supply station. Such signal or alert may for instance be a text message send to the mobile phone of the farmer or a sound emitted in the vicinity of the feeding station.

The system of the present invention may further comprise means for controlling, particularly in an automated manner; the provision of the nutriment the animal or group of animals.

In a particular embodiment the present invention provides a system for monitoring the uptake of a nutriment by a farm bird or group of farm birds according to the method as described above wherein said system comprises
  a) means for acquiring sound and/or vibration data, wherein said vibration data is preferably data on the vibration of said nutriment supply station and/or wherein said sound data is preferably data on the impact sounds transmitted through said feed supply station;
  b) a processing unit adapted to (i) analyse said acquired vibration or sound data, preferably impact sound data, in order to identify and count individual signals, referred to as nutriment uptake signals, resulting from a nutriment uptake action of an animal feeding or drinking from said feed supply station and (ii) to extrapolate the amount of nutriment taken up by said animal or group of animals within a given period of time based on the number of nutriment uptake signals recorded over said same period of time. This extrapolation typically involves the availability in computer readable format of data from preceding experiments wherein for a given type of nutriment, a given type of nutriment supply system and a given species and type of farm bird or farm birds the correlation between the frequency of occurrence of the nutriment uptake signal and the amount of nutriment taken in by the animal or animals is established within a given time interval.

In a preferred particular embodiment of the system of the present invention the nutriment supply station is a feeding pan and the nutriment is a particulate feed. It is further preferred that said vibration data is acquired using an accelerometer mounted on the nutriment supply station, a laser vibrometer pointing at the nutriment supply station or a load cell mounted on the nutriment supply station or that said sound data is acquired using one or more microphones attached to the feeding pan. Optionally, the system of this preferred particular embodiment may further comprise means for monitoring and/or identifying the presence and position of an animal or group of animals within the vicinity of the nutriment supply station.

Another object of the present invention provides a computer program product that includes code segments that when executed on a computer based system of the present invention implements any of the different method embodiments of the present invention described above. Another object of the present invention provides a machine readable storage medium or data carrier storing said above computer program product. Yet another object of the present invention relates to the transmission of said computer program product.

In general, the sound and/or image capture sensors may be set to operate continuously so that said at least one animal is monitored without interruption. However, other set-ups are also contemplated. For instance, the sound and/or image capture sensor may be supplemented with a motion detector sensor so that the either or both of said sensors (and the corresponding sound and/or image processing algorithm) is activated only when an animal enters the nutriment supply station area.

In general said data captured by the sound, vibration and/or image sensors are sent to a processing unit. Said processing unit may also include means for animal identification, to identify the animal or group of animals from which this information was derived. Said sensor(s) may be combined with other sensors (e.g. for measuring feed or animal weight, for detecting and capturing animal movement). For instance, movements of the animal or bird may be detected by one or more movement detectors or one or more cameras.

The present invention implements for the first time a sound and image detection system to define and control the feed or water intake of farm animals. Using the sound and image data alone or in combination with other animal related data, the method and system according to the present invention can be used to determine the feed or water intake of the animal or group of animals, to estimate the feed conversion ratio, predict the growth as well or control the feed supply or to monitor feeding behavior (meal duration, feed swallow interval) or animal welfare. Indeed, in the present method and system each feeding station in the farm might be easily modified by a cheap microphone and webcam or other type of camera to rapidly and correctly in real time calculate the feed intake of the animal, especially farm birds. This is particularly useful in the particular case of commercial broiler farms where a reliable identification of feed intake is vital to reach the right financial evaluation of farm.

In the context of the present invention, a nutriment uptake signal is a signal characteristic of the uptake, consumption, ingestion or attempted ingestion of a nutriment by an animal from a nutriment supply station. Preferably, said nutriment uptake signal results from the impact exerted by the animal on the nutriment supply station when feeding or drinking from said supply station. More preferably, said nutriment uptake signal is a vibration of the nutriment supply station or the sound, preferably the impact sound transmitted through the nutriment supply station, as a result of a nutriment uptake action of an animal feeding or drinking from said nutriment supply station. In the case of farm birds, like poultry, turkeys and the like, said nutriment uptake signal is such vibration or (impact) sound resulting from the pecking of said farm bird when taking up feed from said nutriment supply station. In alternative embodiment, said nutriment uptake signal is correlated to the working of a nutriment supply station. Preferably, in the case of a water supply system, the signal related to the working of the water supply system is an acoustic signal related to the flow of the water in the water supply system or an acoustic signal that marks the start or the end of the drinking period, such as the sound made by the opening or closing of the water tap or drinking nipple.

In the context of the present invention the animal is a livestock or farm animal. Preferably, said farm animal is a farm bird, including but not limited to poultry, turkeys and the like. Alternatively, said farm animal is a mammal, like a cow, pig, and the like.

In the context of the present invention a nutriment means in general any substance that nourishes a living organism, or any substance, that when taken into a living organism, serves to sustain it, or serves to promote its growth, or to provide energy. Preferably, said nutriment is food, animal feed, or water.

Nutriment supply stations, like a feed supply station (e.g. a feeding pan) or a water supply system are well known in the art. Examples of such nutriment supply stations include but are not limited to a feeding pan (for feeding poultry), a trough or manger (for feeding cattle, horses, pigs) or a water or milk (for feeding calves) supply system.

Sound Signal Analysis

This section provides more detailed information on the analysis of the sound data with respect to embodiments of the present invention, which involve the use of an nutriment uptake signal that corresponds to a sound or an impact sound transmitted through the feed supply station wherein said sound results from a nutriment uptake action of an animal feeding or drinking from said nutriment supply station. The procedure as described herein is particularly suited to detect the (impact) sound signal associated with the pecking of farm birds when taking in a particulate feed from a feeding pan. The flow chart for the proposed analysis of acquired sound data for nutriment uptake sound recognition is shown in FIG. 3 and comprises a number of sub processes: (i) Pre-processing (filtering) of the sound signal received from the sound sensors and (ii) Sound signal processing, including sound extraction and sound recognition.

The acoustic signal received by the sound sensors is initially bandpass filtered to eliminate low frequency noise. Preferred cut-off frequencies are about 1 and 5 kHz. A suitable bandpass filter is a Butterworth filter. This is a signal processing filter designed to have as flat frequency response as possible in the bandpass. After bandpass filtering, the signal can be down sampled (e.g. to 11.025 kHz) to reduce processing time.

The signal processing procedure comprises two sub-processes: the sound extraction where individual sounds are extracted from a continuous recording and the sound recognition process where a decision is made whether a sound is recognised as a feed uptake sound, particularly a pecking sound, or other sound.

The extraction of individual sounds from a continuous recording is based on the envelope of the energy of the signal and an automatically selected specific threshold. For instance, the mean value of the envelope over the complete recording can be used for this application. Experimentation suggested that it is adequate for extracting most of the signals that are of interest. However, the noise level and the acoustics of the animal or bird housing & living accommodation affect the resulting signal, and the threshold should be chosen taking them into account. To automatically calculate the envelope of the continuously recorded signal, the Hilbert transform can be used of a discrete time signal k and can for example be defined as $$H\{s[k]\} = \sum_{n=-N/2}^{N/2} s[k-n]h[n]\sin^2\left(\frac{n\pi}{2}\right), \quad (1)$$

where $h[k]=2/(k+\pi)$, for $k=\pm 1, \pm 2, \ldots, \pm N/2$ and $h[0]=0$.

The Hilbert transform provides a 90° phase shift to the original signal and is used according to the following steps: (a) Calculate the energy of the signal; (b) calculate the Hilbert transform of the energy; (c) calculate the square root of the sum of the energy and its Hilbert transform; (d) calculate the moving average of the result to get a smoothed estimate of the envelope of the initial signal.

For sounds to be identified as nutriment (feed) uptake sounds or not, the sum of the power spectral density vector of a signal under consideration is calculated for a frequency range, where the feed uptake sounds, especially pecking sounds, and the other sound signals have considerably different frequency content. Preferably, said frequency range is between 1 and 5 kHz. A threshold value is chosen in the ranges that differentiate the other sound from the feed uptake (pecking) sound signal. Said threshold value can be a fixed threshold, or, preferably, an adaptable threshold, such as for instance 10% of maximum signal. An adaptable threshold is more suitable in case when the frequency contents of feed uptake sounds, especially pecking sounds, and the other sound signals are not stable and not easily distinguishable. In the case of an adaptable threshold, every single sound signal was automatically processed by the system to get a new and right threshold value. After the new threshold was defined, the system is going to classify the sound based on this new threshold. However, the criterion used to recognize a particular sound was the identification of the sudden increase of amplitude in both spectrogram and wave form together with the subsequent decrease. If the sum is below the threshold in the frequency band, the signal is characterised as a feed uptake sound, especially a pecking sound. In general, the durations, frequency ranges and amplitudes of the individual sounds extracted from a continuous recording can be used as classifiers.

The method and system according to the present invention can further comprise one or more of the following:

the use of environmental sensors or local environmental data including temperature, humidity, light levels, . . . . Combining the nutriment uptake sounds with environmental data might give insight in animal behaviour and welfare.

an alert system, allowing immediate feedback to the user, controller or farmer. This can be done by means of any suitable telecommunications method of which SMS (short message service), MMS, email or other information services are only examples.

a server. The information can be put on a server to visualise the feed uptake sounds on animal cage or pen level, on compartment level, on farm level, etc. This can be accessible via internet or a shared server.

welfare monitoring dashboard.

one or more other sensors detecting parameters which can help indicate the animal's behaviour, situation, state of mind and/or identity, including but not limited to physiological sensors (e.g. pheromone detectors; sensors measuring the animal's heart rate, blood pressure, body temperature, etc.; sensors, such as devices generating EEGs or functional MRI scans, which monitor brain activity; etc.), movement sensors (e.g. microwave and passive infrared devices that detect movement wirelessly; sensors linked to devices-hamster wheels and the like-which are operable by the animal; sensors monitoring chips, RFID tags and the like worn by or implanted in the animal; etc.), activity monitors (e.g. accelerometers carried by the animal and counting the number of steps taken).

Implementation

Embodiments of the present invention can comprise control software in the form of a computer program product which provides the desired functionality when executed on a computing device, e.g. a laptop, a personal computer, a mobile phone, a PDA. Further, the present invention can include a data carrier such as a CD-ROM, USB stick or a diskette which stores the computer product in a machine readable form and which executes at least one of the methods of the invention when executed on a computing device. Nowadays, such software is often offered on the Internet or a company Intranet for download, hence the present invention includes transmitting the computer product according to the present invention over a local or wide area network. The computing device may include one of a microprocessor and an FPGA.

The above-described method embodiments of the present invention may be implemented in a processing system (unit) 200 such as shown in FIG. 16. FIG. 16 shows one configuration of processing system 200 that can be implemented on a mobile phone, a PDA, a laptop, a personal computer etc. It includes at least one programmable processor 203 coupled to a memory subsystem 205 that includes at least one form of memory, e.g., RAM, ROM, and so forth. It is to be noted that the processor 203 or processors may be a general purpose, or a special purpose processor, and may be for inclusion in a device, e.g., a chip that has other components that perform other functions. The processor may also be an FPGA or other programmable logic device. Thus, one or more aspects of the present invention can be implemented in digital electronic circuitry, or in computer hardware, firmware, software, or in combinations of them. The processing system may include a storage subsystem 207 that has at least one disk drive and/or CD-ROM drive and/or DVD drive and/or USB port. In some implementations, a display system, a keyboard, and a pointing device may be included as part of a user interface subsystem 209 to provide for a user to manually input information. Ports for inputting and outputting data also may be included, especially interfaces for one or more microphones for capturing sound signals, especially nutriment uptake sounds from an animal or group of animals, particularly farm birds (pecking). Further interfaces may be provided for coupling image capturing devices to the computer system, e.g. for connection to a digital camera or cameras, e.g. a video camera. More elements such as network connections, interfaces to various devices, and so forth, may be included, either by wire line or wireless connections, but are not illustrated in FIG. 6. The various elements of the processing system 200 may be coupled in various ways, including via a bus subsystem 213 shown in FIG. 16 for simplicity as a single bus, but will be understood to those in the art to include a system of at least one bus. The memory of the memory subsystem 205 may at some time hold part or all (in either case shown as 201) of a set of instructions that when executed on the processing system 200 implement the steps of the method embodiments described herein.

The present invention also includes a computer program product, which provides the functionality of any of the methods according to the present invention when executed on a computing device. Such computer program product can be tangibly embodied in a carrier medium carrying machine-readable code for execution by a programmable processor. The present invention thus relates to a carrier medium carrying a computer program product that, when executed on computing means, provides instructions for executing any of the methods as described above. The term "carrier medium" refers to any medium that participates in providing instructions to a processor for execution. Such a medium may take many forms, including but not limited to, non-volatile media, and transmission media. Non volatile media includes, for example, optical or magnetic disks, such as a storage device which is part of mass storage. Common forms of computer readable media include, a CD-ROM, a DVD, a flexible disk or floppy disk, a tape, a memory chip or cartridge or any other medium from which a computer can read. Various forms of computer readable media may be involved in carrying one or more sequences of one or more instructions to a processor for execution. The computer program product can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fibre optics, including the wires that comprise a bus within a computer.

Example 1. Identification of Broiler Pecking Sounds

Birds and Housing

In total, 36 experiments were conducted to 12 male, 28 days old Ross 308 broilers. Birds were kept on floor pens on wood shavings. Feed and water were freely available to bird during the experiments. Birds were allowed of two days to recover from the stress of transport and to acclimatize to their new environment. Lights were kept on during the sound and video recordings.

Experimental Setup

Every following day a different individual broiler chicken was used in the experiment. In total, three experiments were performed for each individual broiler. In the experiments, all sounds (pecking, singing and environmental sounds such as ventilation) inside the laboratory were continuously recorded during 15 minutes.

For the sound recording, an electret microphone (Monacor ECM 304BD) was attached under the feeding pan, i.e. attached to the external side of the bottom of the feeding pan, during the experiments. It had a frequency response of 30-20,000 Hz and was connected to PC via preamplifier (Monacor SPR-6). The position of the microphone is shown in FIG. 1. All recordings were sampled at a sample rate of 44.1 kHz with a resolution of 16 bit. The sound data were processed with Matlab (Mathworks). For the validation of the system results, all images were captured by a USB webcam (Logitech Webcam Pro) mounted next the cage at far of 50 cm and with its lens pointing towards the cage to get a side view of the feeder (FIG. 1). The webcam captured images with a resolution of 640 horizontal by 480 vertical pixels at a sample rate of 15 frames per second. The image data were manually labelled using the labelling tool developed by Leroy et al. (2005, ASAE 2005 Annual meeting). For the second validation of the proposed system, a weighing system (KERN PCB-250-3, Precision Balance with weighing range 250 g and accuracy 0.001 g) was used. The feeding pan was placed on this weighing system, which is connected to the PC via RS-232 cable. Weighing data is continuously (10 times per second) transferred and recorded to the PC by Matlab (Mathworks).

Pre-Processing of the Signal—Definition of the Frequency Ranges

Before the extraction part of the system was applied, the complete recording was pre-processed. Subsequently, the individual sounds (pecking and other sounds) were manually extracted from the continuous recordings and stored as individual sounds. Therefore, the generated data set includes individual sounds of 100 pecking and 100 other sounds (that include chick vocalisations and environmental sounds) to define the best frequency band which is including the most different frequency ranges between the pecking and other sounds.

Pre-Processing of the Signal—Filtering

To eliminate low frequency noise produced mainly by the ventilation installation in laboratory, and since the pecking sound signals that need to be recognized do not have considerable low frequency components, the signal is initially bandpass filtered. For this, the signals were band pass-filtered (6th order Butterworth filter) with cut-off frequencies of 1 and 5 kHz. Although the sounds of broiler chickens show frequencies up to 5 kHz, the frequency range between 1 kHz and 5 kHz holds enough information for the purpose of this idea. By applying the lower cut-off frequency of 1 kHz, the low frequency noise in the signal has been removed. FIG. 2 shows the filtered sound signal between 1 kHz and 5 kHz.

The Butterworth filter is a signal processing filter designed to have as flat frequency response as possible in the bandpass. After bandpass filtering, the signal was down sampled from 44.1 to 11.025 kHz to reduce processing time. The flowchart for the proposed signal processing procedure is shown in FIG. 3.

The signal processing procedure comprises two subprocesses: the sound extraction where individual sounds are extracted from a continuous recording and the sound recognition process where a decision is made whether a sound is recognised as pecking sound or other sound.

Subprocess 1: Sound Extraction

The extraction of individual sounds from a continuous recording is based on the envelope of the energy of the signal and an automatically selected specific threshold. The mean value of the envelope over the complete recording is used for this application assuming that it is adequate for extracting most of the signals that are of interest. To automatically calculate the envelope of the continuously recorded signal, the Hilbert transform of a discrete time signal k can be defined as $$H\{s[k]\} = \sum_{n=-N/2}^{N/2} s[k-n]h[n]\sin^2\left(\frac{n\pi}{2}\right), \quad (1)$$

where $h[k]=2/(k+\pi)$, for $k=\pm 1, \pm 2, \ldots, \pm N/2$ and $h[0]=0$ The Hilbert transform provides a 90° phase shift to the original signal and is used according to the following system: Calculate the energy of the signal, calculate the Hilbert transform of the energy, calculate the square root of the sum of the energy and its Hilbert transform, and calculate the moving average of the result to get a smoothed estimate of the envelope of the initial signal.

The result of this procedure is presented in FIG. 4, where a continuous recording of sounds is presented and the extracted pecking sounds are shown.

Subprocess 2: Sound Classification

For sounds to be identified as pecking or not, the sum of the power spectral density vector of a signal under consideration is calculated for a frequency range between 1 and 5 kHz. The frequency range was identified where the pecking and the other sound signals have considerably different frequency content. Based on this, the threshold value can be chosen in the ranges that differentiate the other sound from the pecking sound signal. In this research, an adaptable threshold (10% of maximum signal) was chosen instead of the fixed threshold, due to the frequency contents of pecking and other sound signals, which are not stable and not easily distinguishable. Every single sound signal was automatically calculated by the system to get a new and right threshold value. After the new threshold was defined, the system is going to classify the sound based on this new threshold. However, the criterion used to recognize a particular sound was the identification of the sudden increase of amplitude in both spectrogram and wave form together with the subsequent decrease. FIG. 5 shows a spectrogram of a continuous sound consisting of several individual pecking. If the sum is below the threshold in the frequency band, the signal is characterised as a pecking.

Accuracy of the system to detect broiler pecking sounds is an important parameter. All sounds were processed and identified as pecking or other sound by using the proposed system. Table 1 shows the total number of pecking sounds identified by the system and the total number of pecking sounds identified by labelling. False positives, were obtained when a sound of other nature were falsely identified as pecking. The false positives classified as other sounds were presented in Table 1. In the experimental setup, 92.97% of the pecking were correctly identified (i.e. 7.03% of false positive results).

TABLE 1

Results of identification of pecking sounds during feed intake.

| Data Set | Number of pecking (System) | Number of pecking (Video Labelling) | Accuracy of System (%) | True Positive | False Positive |
| --- | --- | --- | --- | --- | --- |
| 1 | 113 | 105 | 93.2 | 105 | 8 |
| 2 | 99 | 95 | 96.2 | 95 | 4 |
| 3 | 109 | 106 | 97.6 | 106 | 3 |
| 4 | 98 | 91 | 92.9 | 91 | 7 |
| 5 | 97 | 88 | 90.6 | 88 | 9 |
| 6 | 105 | 95 | 90.2 | 95 | 10 |
| 7 | 105 | 99 | 94.5 | 99 | 6 |
| 8 | 97 | 92 | 94.9 | 92 | 5 |
| 9 | 107 | 98 | 91.7 | 98 | 9 |
| 10 | 105 | 97 | 92.2 | 97 | 8 |
| 11 | 104 | 94 | 90.6 | 94 | 10 |
| 12 | 108 | 100 | 92.9 | 100 | 8 |
| 13 | 99 | 91 | 91.7 | 91 | 8 |
| 14 | 96 | 90 | 93.3 | 90 | 6 |
| 15 | 112 | 108 | 96.8 | 108 | 4 |
| 16 | 109 | 98 | 90.3 | 98 | 11 |
| 17 | 100 | 91 | 91.4 | 91 | 9 |
| 18 | 103 | 97 | 94.4 | 97 | 6 |
| 19 | 105 | 95 | 90.3 | 95 | 10 |
| 20 | 108 | 99 | 91.3 | 99 | 9 |
| 21 | 97 | 89 | 92.3 | 89 | 8 |
| 22 | 96 | 89 | 92.7 | 89 | 7 |
| 23 | 96 | 88 | 91.4 | 88 | 8 |
| 24 | 99 | 95 | 96.4 | 95 | 4 |
| 25 | 103 | 96 | 93.2 | 96 | 7 |
| 26 | 95 | 89 | 93.2 | 89 | 6 |
| 27 | 108 | 100 | 92.2 | 100 | 8 |
| 28 | 107 | 101 | 94.4 | 101 | 6 |
| 29 | 109 | 102 | 93.3 | 102 | 7 |
| 30 | 106 | 100 | 94.4 | 100 | 6 |
| 31 | 102 | 93 | 91.3 | 93 | 9 |
| 32 | 103 | 95 | 91.9 | 95 | 8 |
| 33 | 107 | 100 | 93.7 | 100 | 7 |
| 34 | 107 | 101 | 94.4 | 101 | 6 |
| 35 | 98 | 91 | 93.3 | 91 | 7 |
| 36 | 95 | 88 | 92.35 | 88 | 7 |
| Total-Average | 3707 | 3447 | 92.97 | 3447 | 7 |

Example 2. Detection of Feeder Visits and Counting Animals at Feeder

Image Analysis

As an input to the sound processing system and also to improve the accuracy of detection of feeding visits, counting number of animals at the feeder and calculating how long each animal stays at a feeder, an image analysis system can be added. The processing flowchart to detect animals at a feeder is as follows (FIG. 6). The first step is to subtract background from the image. Second is to segment the image to localize the animals. Third is to model the animal's body appeared in the resulted image. This can be a geometrical shape such as an ellipse or a mathematical model describing body shape or border. Fourth is to detect direction of animals. This can be attained by analyzing geometrical features of the model parameters and calculating distances of geometrical model locations with the feeder position. Finally, duration of feeding can be monitored and recorded. Information retrieved using this process can be compared with results of sound processing.

This image analysis system consists of the following processing stages: (i) Background subtraction; (ii) Fitting models (elliptic for example) to individual animals; (iii) Calculating duration of visits per individual. Below these steps are explained in details.

(i) Background Subtraction

The first step in detection of animals is to subtract the background to be able to focus on objects in the image. Here the process is explained in an example of a broiler house. FIG. 7 shows a top-view image of a feeder in a broiler house.

In the first step, the image is binarised to eliminate the background. The binarisation procedure is as follows. First, the image is filtered using a 2-D Gaussian low-pass filter. Then, a global threshold is calculated using Otsu's method (Otsu, 1979). Next, the image is hard-thresholded. To remove small objects from the image, a morphological closing operator using a disk-shaped structuring element with size of 10 pixels (Gonzalez and Woods, 2001) is performed on it, resulting in FIG. 8.

(ii) Fitting Elliptic Models to Individual Animals

To localize the broilers and count them, broilers' bodies are extracted as simple models, such as ellipses (Zhang et al., 2005; Tillett, 1991): bright regions relate to the broiler's bodies and they have a rather high contrast with the background (house floor). The procedure for fitting ellipses to the binary image of FIG. 8 makes use of the region props function in MATLAB, and object parameters such as Orientation, MajorAxisLength, MinorAxisLength and Centroid for all objects in the image are calculated. To avoid taking other shapes in the image mistakenly as broilers, a minimum and a maximum of pixels for major and minor axes of an ellipse are considered. FIG. 9 shows the ellipses fitted to each broiler.

(iii) Calculating Duration of Visits Per Individual

Based on FIG. 10, a visit is detected when the angle (θ) between the line passing through the feeder's center (A) and closest point on the ellipse intersecting its own major axis (B) to point A is convex and the distance between points A and B is below a threshold. Duration of visits is recorded and used for improving feed intake estimation in combination with sound analysis.

Implementation

Hardware requirements of the image processing system discussed above include only one camera installed above each feeder and a PC with a video capture card with suitable interfaces to read out camera data.

Example 3. Broiler Feed Intake

The feed intake is the quantity (g) of feed ingested by chickens with each pecking. This value was calculated subtracting the feed loss (quantitative (g) of feed spilled to ground) from the feed uptake (quantitative (g) of feed removed from feeding pen by chicken with each pecking). The feed uptake of chickens were automatically defined by sound algorithm and continuously recorded by a weighing system while the feed losses were collected and recorded manually after each experiment (see tablet).

The feed intake per experiment (FIPE) is therefore defined as:

$$FIPE = FUPE - FLPE \quad (1)$$

This equation corresponds to the difference between the total feed uptake per experiment (FUPE) and the total feed loss per experiment (FLPE).
Calculation of the average feed intake per pecking (FIPP) is defined as;

$$FIPP = \frac{FIPE}{NPPE} \quad (2)$$

This equation corresponds to the ratio between the total feed intake per experiment (FIPE) and the total number of pecking per experiment (NPPE). The number of peckings can be identified using the method of example 1.

Next, image analysis was employed to discover how many broilers are eating at the same time. This helps to increase the accuracy of feed intake estimation since competition between animals and the age of animals can be considered and compensated.

Before estimating the absolute amount of feed intake of chickens from pecking sounds algorithm, the relations between the number of peckings and feed uptake of chickens were investigated. A linear relation was found between the variables (see FIG. 11). All sound data were again analysed with an interval of one minute and compared to feed uptake per minute to be sure the strength of the linear relationship between the variables (see FIG. 12). Afterwards, the linear regression test was performed and the coefficient of determination ($R^2$), was found as 0.995 (see FIG. 12).

Furthermore, the results of individual feed intake per pecking were statistically compared. The results show that there are not significant differences between the feed intake of individual chickens (see table 3).

TABLE 3

Statistical test results of the feed intake of chickens.

| Source of Variation | Sum of Squares (SS) | Degrees of freedom (df) | Mean Square (MS) | F Value | Prob > F |
|---|---|---|---|---|---|
| Columns | 1.82E−006 | 11 | 1.66E−01 | 1.06 | 0.44 |
| Error | 3.80E−005 | 24 | 1.58E−01 | | |
| Total | 5.62E+005 | 35 | | | |

The statistical results presented here indicate that there is not significant differences between the feed intake of chickens. It means that the amount of feed intake of chickens can be estimated from the number of peckings, which can be automatically identified by a sound analysis algorithm.

However, to develop the proposed algorithm to work under field conditions, a number of technical challenges have to be overcome. The most important of these challenges was that each feeding pan in farm might be easily modified by a very cheap microphone to rapidly and correctly calculate the feed intake of chickens.

In conclusion, in examples 1, 2 and 3, a novel system for fully automated recognition of broiler pecking sounds was developed. Sound recordings from pecking birds were recorded and compared to measurements by a weighing system and video observations. In addition, a camera was installed on the top of the feeders. Images collected by cameras were analysed on a processing unit connected to the cameras. The number of animals at the feeder and duration of visits were reported to the sound analysis system. Contrary to previous studies in literature (Ungar and Rutter, 2006, Appl. Animal Behaviour Sci, 98: 11-27; Galli et. al., 2005, Animal Feed Sci Technol, 128, 14-30) a very cheap microphone was attached to the feeding pan which is much easier than an attachment to each animal, especially in the case of farm birds. The instantaneous energy of the signal was used to detect and extract individual sounds from a continuous recording. Their durations, density, frequency ranges and amplitudes were used as classifiers. The results show that the majority of sounds were identified correctly as pecking' and false positives were kept to a minimum, thus allowing for a highly accurate broiler pecking sound detection. The results showed that there was not a significant differences (F=0.44) between the feed intake of chickens (see table 3). It means that the absolute amount of feed intake of chickens can be defined with this system using by combination of sound and image technology.

The real-time dynamic sound data of feed uptake provide an important basis for monitoring and controlling broiler feeding behaviour and welfare. For example, distribution of animals around feeding and drinking lines in poultry house could be estimated by this system in real time. Beside that the number of animals around a feeding pen could be calculated by this system and with these information, the size and weight of chickens could be estimated.

On the other hand, the particle size of different feed components inside the feeding pen could be estimated and the homogeneity of feed (e.g. grain vs. powder) could be monitored by calculating a feature of the sound signal in this system.

Example 4. Estimation of Water Intake

The drinking nipples were manually opened and closed; the resulting sound was measured in two microphones with a sample frequency of 22.050 Hz. Two microphones were used in the experiment: microphone 1 is positioned at the drinking nipple itself, while microphone 2 is positioned on the water tube (perpendicular mounting on the water tube).

The start and the end of the drinking period are determined automatically, based on the acoustic signals that are captured. When the drinking nipple is opened or closed, the microphones pick up a clear clicking sound that is produced by the nipple movement.

In another experimental setup, water intake of animals was estimated based on acoustic signals measured by simple microphones. FIG. 14 shows the variation in sound pressure level in microphone 1 (at the drinking nipple), respectively microphone 2 (on the water tube).

When the drink nipple opens and closes, there is a clear sound click produced by the nipple. These open and close clicks of drinking nipple are clearly visible as peaks that come well above the average rms value of the sound (see FIG. 14). Based on simple threshold techniques, begin (T1) and end (T2) of a drinking period are determined in an automated way. Based on the water flow (which is assumed to be known a priori; this can easily be measured in practice, see*), the start and end of a drinking period and the water intake of the animal can for example be estimated as:

Water intake [liter]=drinking efficiency [liter drunk by the animal/litter through the drinking nipple] *(T2−T1) [seconds]·*Flow [liter/second].

The drinking efficiency is assumed to be constant and is a value between 0 and 1. When FIGS. 14 and 15 are compared, it is clear that the time signal of the recorded sounds fits to instantaneous water flow. FIG. 15 shows the cumulative and instantaneous water flows through water meter sensors. In the latter figure; it is clear that the sensor's maximal flow is reached.

In conclusion, the described measurements show that the water intake of animals can be estimated based on the water flow through the system (assumed to be constant) and by using acoustic signals for begin- and end detection of the drinking periods.

In case the water flow is not known, a simple measurement can give the required information: opening the drinking nipple for time T and capturing the amount of water that comes out of the nipple with a measurement container.

Flow [liter per second]=Amount of water [liter]/time $T$ [seconds])

The invention claimed is:

1. An automated method for monitoring the amount of a nutriment taken up by an animal or group of animals feeding or drinking from a nutriment supply station wherein said method comprises the steps of:
    acquiring data on the vibration of said nutriment supply station and/or on the impact sounds transmitted through said feed supply station;
    analyzing said vibration or impact sound data in order to identify and count individual nutriment uptake signals, resulting from a nutriment uptake action of an animal feeding or drinking from said nutriment supply station; and
    extrapolating the amount of nutriment taken up by said animal or group of animals within a given period of time based on the number of nutriment uptake signals recorded over said same period of time.

2. The method according to claim 1 wherein the impact sounds transmitted through said feed supply station are acquired using a microphone mounted on the nutriment supply station.

3. The method according to claim 1 wherein data on the vibration of the nutriment supply station are acquired using an accelerometer mounted on the feed supply station.

4. The method according to claim 1 wherein data on the vibration of the nutriment supply station are acquired using a laser vibrometer pointing at the feed supply station.

5. The method according to claim 1, wherein the analysis of the vibration and/or impact sound data is done in real time.

6. The method according to claim 1, further comprising monitoring and/or identifying the presence and position of said animal or group of animals within the vicinity of the nutriment supply station.

7. The method according to claim 6 wherein the presence and position of an animal at the nutriment supply station is identified and/or monitored using a camera capturing images of the nutriment supply station and/or its vicinity and means for analyzing the images captured by said camera.

8. The method according to claim 7 wherein the analysis of the image data is combined with the analysis of said vibration and/or impact sound data.

9. The method according to claim 8 wherein said analysis of the image data is combined with the analysis of said vibration and/or impact sound data occurs in real time or semi-real time.

10. The method according to claim 1, wherein said nutriment is a solid feed, a particulate feed, a liquid feed or water and/or wherein said nutriment supply station is a feed supply station, a feeding pan, a feeding trough or a water supply system.

11. The method according to claim 1 wherein said animal is a farm animal.

12. The method according to claim 11 wherein said nutriment is a particulate feed and wherein said nutriment uptake signal is a vibration of the feed supply station and/or an impact sound transmitted in the feeding supply station as a result of the pecking of said farm bird when taking up feed from said feed supply station.

13. The method according to claim 12 wherein said feed supply station is a feeding pan.

14. The method according to claim 13 wherein impact sounds transmitted through the feeding pan are acquired using a microphone attached to said feeding pan and/or wherein the vibrations of the feeding pan are acquired using an accelerometer or laser vibrometer.

15. The method according to claim 1 further comprising the step of generating an alert or signal to said animal or group of animals and/or to the controller and/or the method further comprising the step of (automated) controlling the provision of nutriments to said animal or group of animals and/or wherein the analysis of the impact sound data for the identification and counting of said nutriment uptake signals comprises a sound extraction step and a sound recognition step.

16. The method according to claim 6 wherein the image analysis comprises an image background subtraction, ellipse fitting and geometrical image analysis step.

17. A system for monitoring the uptake of a nutriment by an animal or group of animals according to the method of claim 1 wherein said system comprises
    means for acquiring data on the vibration of said feed supply station and/or on the impact sounds transmitted through said feed supply station;
    a processing unit adapted to (i) analyse said acquired vibration or impact sound data in order to identify and count individual nutriment uptake signals, resulting from a nutriment uptake action of an animal feeding or drinking from said feed supply station and (ii) to extrapolate the amount of nutriment taken up by said animal or group of animals within a given period of time based on the number of nutriment uptake signals recorded over said same period of time.

18. The system according to claim 17 further comprising means for sensing the presence and/or position of the animal or group of animals within the vicinity of the nutriment supply station and wherein said processing unit is adapted to analyse said sensed input.

19. The system according to claim 17, wherein said means for acquiring data on the vibration of said feed supply station and/or on the impact sounds transmitted through said feed supply station is an accelerometer, a laser vibrometer, load cell or a microphone and/or wherein said means for sensing the presence and/or position of the animal is a camera, adapted or located to provide a top-view image of said nutriment supply station and/or the vicinity thereof.

20. A computer program product for, if implemented on a control or processing unit of a system for monitoring the uptake of a nutriment by an animal or group of animals according to the method of claim 1 wherein said system comprises:

means for acquiring data on the vibration of said feed supply station and/or on the impact sounds transmitted through said feed supply station;

a processing unit adapted to (i) analyse said acquired vibration or impact sound data in order to identify and count individual nutriment uptake signals, resulting from a nutriment uptake action of an animal feeding or drinking from said feed supply station and (ii) to extrapolate the amount of nutriment taken up by said animal or group of animals within a given period of time based on the number of nutriment uptake signals recorded over said same period of time.

* * * * *